United States Patent
Fridman et al.

(10) Patent No.: US 10,674,922 B2
(45) Date of Patent: Jun. 9, 2020

(54) DEVICE AND METHOD FOR FAST ACQUISITION OF VITAL SIGNS

(71) Applicant: THE JOHNS HOPKINS UNIVERSITY, Baltimore, MD (US)

(72) Inventors: Gene Yevgeny Fridman, Baltimore, MD (US); Yang Hong, Baltimore, MD (US); Hai Tang, Baltimore, MD (US)

(73) Assignee: Aidar Health, Baltimore, MD (US)

(*) Notice: Subject to any disclaimer, the term of this patent is extended or adjusted under 35 U.S.C. 154(b) by 86 days.

(21) Appl. No.: 15/567,744

(22) PCT Filed: Apr. 20, 2016

(86) PCT No.: PCT/US2016/028330
§ 371 (c)(1),
(2) Date: Oct. 19, 2017

(87) PCT Pub. No.: WO2016/172132
PCT Pub. Date: Oct. 27, 2016

(65) Prior Publication Data
US 2018/0110418 A1    Apr. 26, 2018

Related U.S. Application Data

(60) Provisional application No. 62/149,740, filed on Apr. 20, 2015.

(51) Int. Cl.
*A61B 5/0205* (2006.01)
*A61B 5/024* (2006.01)
(Continued)

(52) U.S. Cl.
CPC .......... *A61B 5/0205* (2013.01); *A61B 5/0006* (2013.01); *A61B 5/0022* (2013.01);
(Continued)

(58) Field of Classification Search
CPC .... A61B 2560/0223; A61B 2560/0431; A61B 5/0006; A61B 5/0022; A61B 5/01;
(Continued)

(56) References Cited

U.S. PATENT DOCUMENTS

| 4,413,629 A | 11/1983 | Durley, III |
| 6,190,326 B1* | 2/2001 | McKinnon ........... A61B 5/0871 128/200.24 |

(Continued)

FOREIGN PATENT DOCUMENTS

| WO | 2004012577 A2 | 2/2004 |
| WO | 2012108895 A1 | 8/2012 |

OTHER PUBLICATIONS

International Search Report and The Written Opinion of the International Searching Authority, International Application No. PCT/US/2016/028330, dated Jul. 25, 2016.

*Primary Examiner* — Michael W Kahelin
*Assistant Examiner* — Vynn V Huh
(74) *Attorney, Agent, or Firm* — Murtha Cullina LLP; Anthony P. Gangemi

(57) ABSTRACT

The present invention is directed to a self-contained hand-held device that obtains vital signs accurately, simultaneously, comfortably, and quickly. Unlike currently used devices that require trained personnel and the attachment of sensors to the different parts of the patient's body, this device can obtain all vital signs +ECG and pulse-ox by being held by the patient for approximately half a minute. The device contains sensors on the hand-held unit as well as on the individual/disposable mouthpiece. The method of the present invention includes simultaneously acquiring the following measurements: temperature, pulse rate, breathing rate, blood pressure, electrocardiogram, and pulse-ox waveform and blood oxygen level.

17 Claims, 9 Drawing Sheets

(51) Int. Cl.

| | |
|---|---|
| *A61B 5/145* | (2006.01) |
| *A61B 5/00* | (2006.01) |
| *A61B 5/08* | (2006.01) |
| *A61B 5/01* | (2006.01) |
| *A61B 5/0404* | (2006.01) |
| *A61B 5/1455* | (2006.01) |
| *G16H 10/40* | (2018.01) |
| *G16H 40/63* | (2018.01) |
| *A61B 5/021* | (2006.01) |
| *A61B 5/0402* | (2006.01) |
| *A61B 5/04* | (2006.01) |

(52) U.S. Cl.
CPC ............. *A61B 5/01* (2013.01); *A61B 5/021* (2013.01); *A61B 5/02405* (2013.01); *A61B 5/02438* (2013.01); *A61B 5/0404* (2013.01); *A61B 5/082* (2013.01); *A61B 5/0816* (2013.01); *A61B 5/14507* (2013.01); *A61B 5/14532* (2013.01); *A61B 5/14551* (2013.01); *A61B 5/4866* (2013.01); *A61B 5/682* (2013.01); *A61B 5/7278* (2013.01); *A61B 5/742* (2013.01); *G16H 10/40* (2018.01); *G16H 40/63* (2018.01); *A61B 5/0402* (2013.01); *A61B 5/04004* (2013.01); *A61B 2560/0223* (2013.01); *A61B 2560/0431* (2013.01)

(58) Field of Classification Search
CPC ... A61B 5/0205; A61B 5/021; A61B 5/02405; A61B 5/02438; A61B 5/04004; A61B 5/0402; A61B 5/0404; A61B 5/0816; A61B 5/082; A61B 5/14507; A61B 5/14532; A61B 5/14551; A61B 5/4866; A61B 5/682; A61B 5/7278; A61B 5/742; G16H 10/40; G16H 40/63
USPC .................................. 600/300–301
See application file for complete search history.

(56) References Cited

U.S. PATENT DOCUMENTS

| | | | |
|---|---|---|---|
| 2006/0064037 A1* | 3/2006 | Shalon | A61B 5/0006 600/586 |
| 2008/0216831 A1 | 9/2008 | McGinnis et al. | |

* cited by examiner

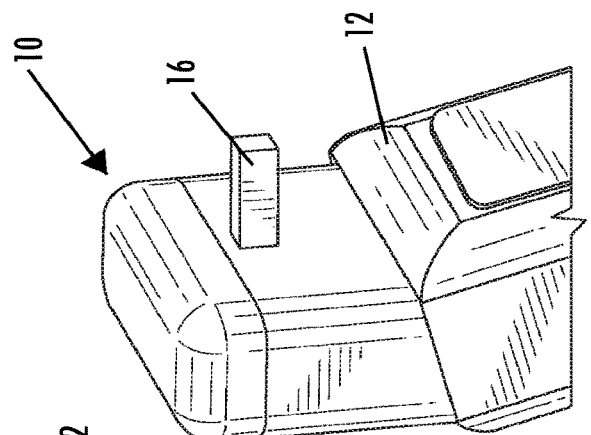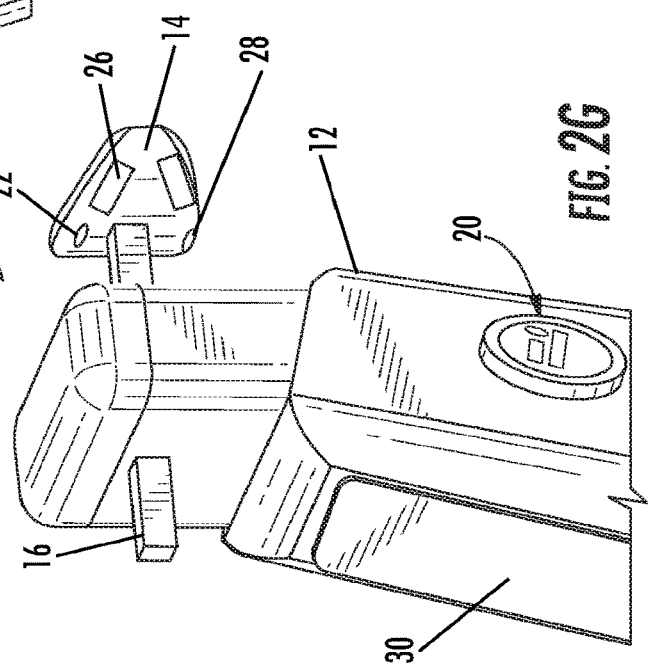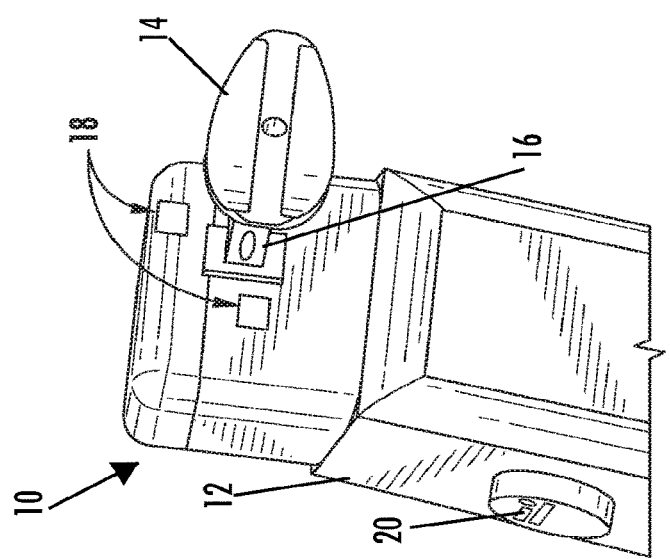

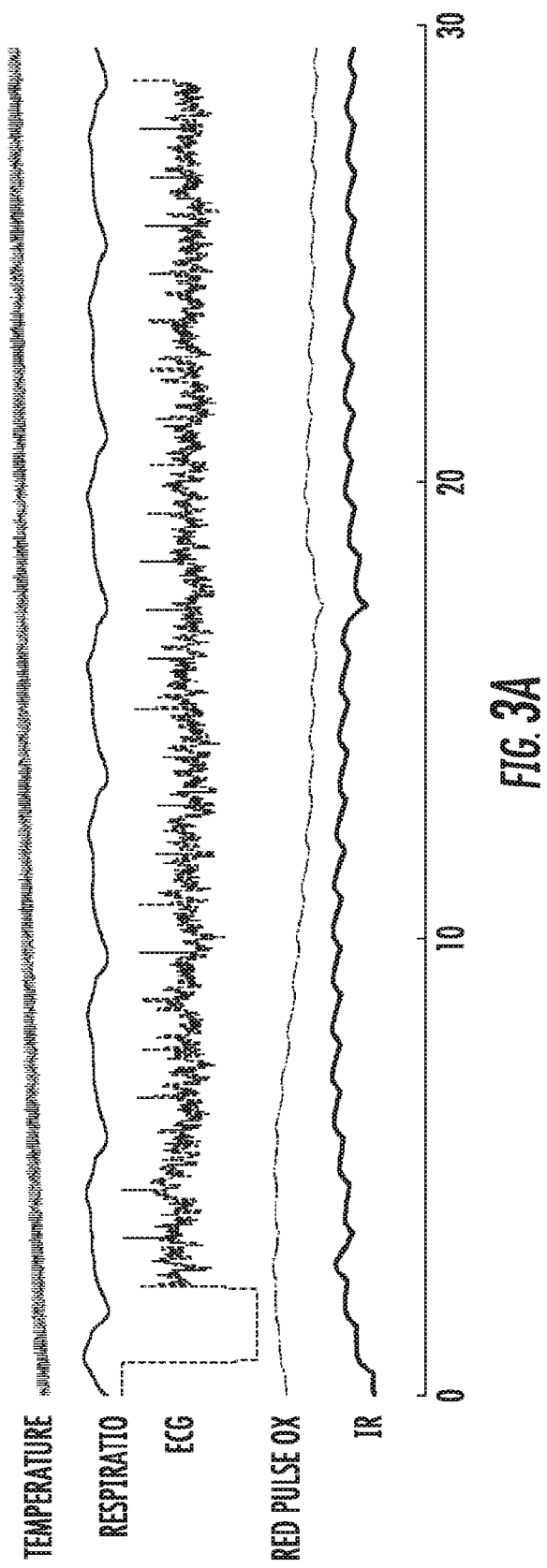

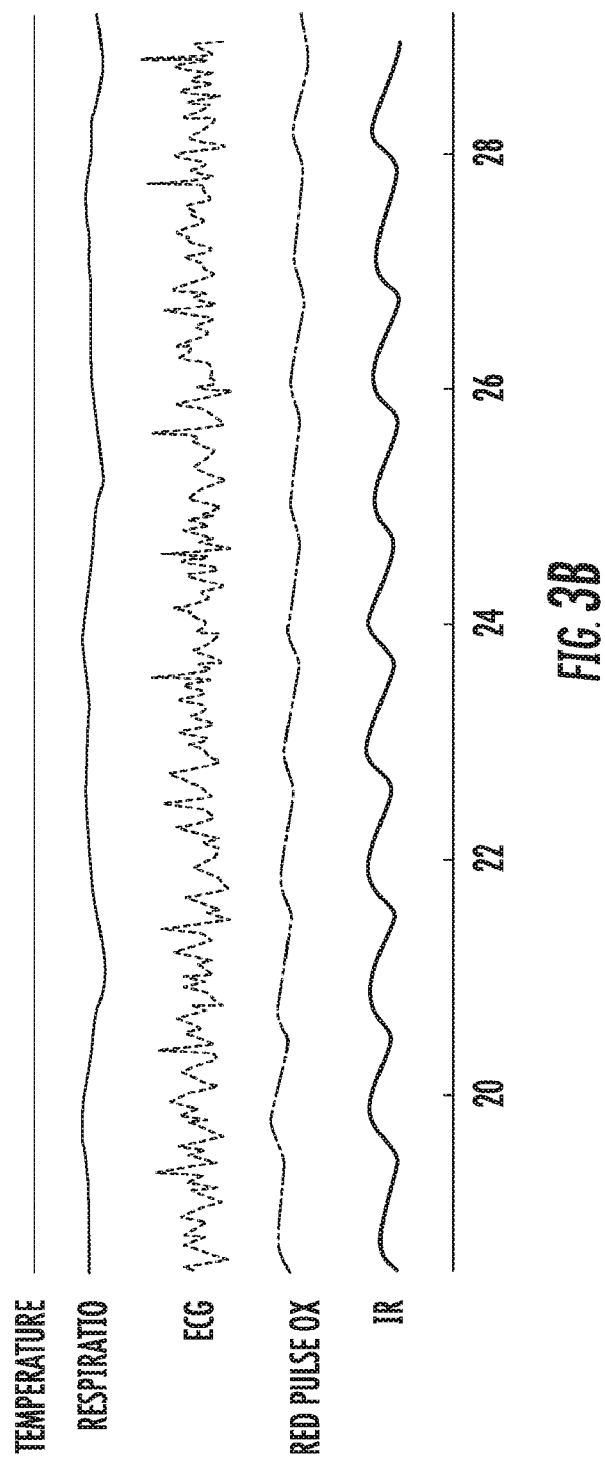

DEVICE AND METHOD FOR FAST ACQUISITION OF VITAL SIGNS

CROSS REFERENCE TO RELATED APPLICATIONS

This application is a National Stage filing of International Application No. PCT/US2016/028330, filed Apr. 20, 2016, which claims the benefit of U.S. Provisional Patent Application No. 62/149,740 filed Apr. 20, 2015, which is incorporated by reference herein, in its entirety.

FIELD OF THE INVENTION

The present invention relates generally to a medical device. More particularly, the present invention relates to a device and method for fast acquisition of vital signs.

BACKGROUND OF THE INVENTION

Currently, in order to obtain vital signs from a person multiple devices are needed. Additionally, many of the vital sign measurements also require a trained professional in order to achieve accurate results. Therefore, a person who requires periodic vital sign checks must visit a clinic or a hospital, find a trained technician, and or acquire a number of devices designed for obtaining the necessary vital sign measurements.

It would therefore be advantageous to provide a device and a method for measuring vital signs quickly and accurately in an integrated device that can be used without the assistance of a skilled technician, physician, or nurse.

SUMMARY OF THE INVENTION

The foregoing needs are met by the present invention which provides a device for measuring vital signs including a device body having an on/off switch and a user display. The device includes a mouthpiece that is coupled to the device body. The device also includes a connector for coupling the mouthpiece to the device body, wherein the connector is saliva insulated, and attached the mouthpiece to the device body both electrically and physically. The device also includes a sensor for determining vital signs.

In accordance with an aspect of the present invention, the device is further configured to determine at least one of the vital signs selected from a group of breathing rate, blood pressure, temperature, electrocardiogram, pulse rate, blood oxygen levels, blood sugar levels, respiration biochemical analysis, saliva biochemical analysis, and metabolic rate. The sensor at least one selected from a group of a microphone, ECG−, ECG+. ECGref, optodetector, IR LED, RED, and thermocouple. The on/off switch includes an ECG+ contact, an RED, IR LED, and an optodetector. The mouthpiece includes an ECG− contact, an ECGref contact, an upper lip optodetector, and an IR LED. The microphone is positioned on the device body. The device includes a computing device with a non-transitory computer readable medium programmed to store and transmit data related to the vital signs. The computing device is networked to a smartphone for transmitting data to a server for processing. The data transmitted to the server is further transmitted to a computer application for use by a physician. The display is configured to show at least one selected from a group consisting of instructions, data acquisition time required, results, and testing being completed.

In accordance with another aspect of the present invention, the user display is incorporated into the device body. Alternately, the user display takes the form of a separate computing device configured to transmit information to and receive information from the device for measuring vital signs. The microphone is configured to be set with one sensitivity. Alternately, a pair of microphones can have different sensitivities or a microphone can have variable sensitivities. The sensor is configured to collect data from the mouth. A second sensor can be used to collect data from an appendage. The microphone further includes a high-dynamic range microphone. The device can also include a high-dynamic range analog to digital converter.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 2E illustrates a front-perspective view of the device, according to an embodiment of the present invention.

FIG. 2F illustrates a side view of the device, according to an embodiment of the present invention.

FIG. 2G illustrates a rear-perspective view of the device according to an embodiment of the present invention.

FIG. 3A illustrates a graphical view of a sample of typical data collected by sensors on a device according to an embodiment of the present invention.

FIG. 3B illustrates a graphical view of a portion of the recording in greater detail.

DETAILED DESCRIPTION

Figure 1:
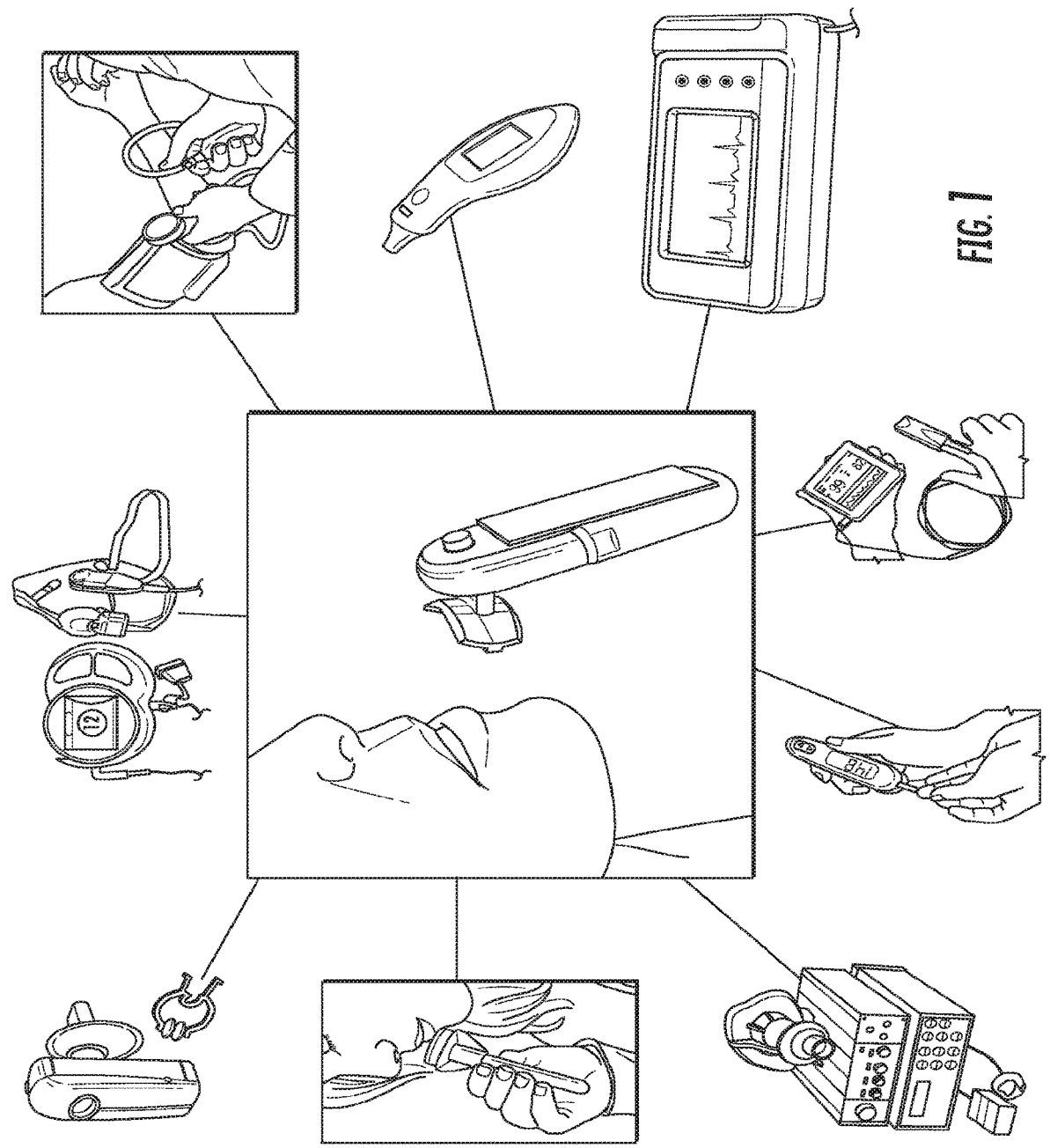
FIG. 1 illustrates a schematic diagram of the device, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a self-contained hand-held device that obtains vital signs accurately, simultaneously, comfortably, and quickly. Unlike currently used devices that require trained personnel and the attachment of sensors to the different parts of the patient's body, this device can obtain all vital signs +ECG and pulse-ox by being held by the patient for approximately half a minute. The device contains sensors on the hand-held unit as well as on the individual/disposable mouthpiece. The method of the present invention includes simultaneously acquiring the following measurements: temperature, pulse rate, breathing rate, blood pressure, electrocardiogram, and pulse-ox waveform and blood oxygen level. It should be noted that the device will be described herein as MouthLab.

The positioning of the sensors on the device to allow simultaneous acquisition of the medical parameters is novel. The method of acquiring blood pressure is novel, as is the method of acquiring pulse oximetry waveform and the ECG. The key feature that differentiates this device from other solutions is the use of the patient's thumb and the lip for biomedical measurements, rather than the parts of the mouth alone. The lip and the thumb are separated by a significant distance on the body. This distance allows the ECG signals to be large and the difference in blood flow measurements to be considerably different between the lip and the thumb. Acquisition of the metrics from the mouth and thumb significantly improves the reliability and quality of the ECG and blood pressure measurements over acquisition from the mouth alone.

MouthLab enables patients themselves to make more accurate measurements in less time. Because MouthLab is digital, there is no transcription of results required, leading to fewer errors in reported values. MouthLab measures vital signs, including, but not limited to, temperature, pulse rate, respiratory rate, blood pressure, ECG, and blood oxygen. The platform can also support measuring blood sugar level for diabetics and measuring breathing patterns, and saliva and respiratory biochemistry to aid in illness recovery monitoring and diagnosis.

FIG. 1 illustrates a schematic diagram of the device, according to an embodiment of the present invention. FIG. 1 includes the device and a listing of some of the vital signs that the device is able to determine for the user. The listing of vital signs is not meant to be limiting and the device can be configured to measure and determine vital signs that are not included herein, but are known to or conceivable by one of skill in the art. As illustrated in FIG. 1, the device can measure metabolic rate, breathing rate, blood pressure, temperature, electrocardiogram and pulse rate, blood oxygen level, blood sugar level, respiration biochemical analysis, and saliva biochemical analysis.

Figure 2C:
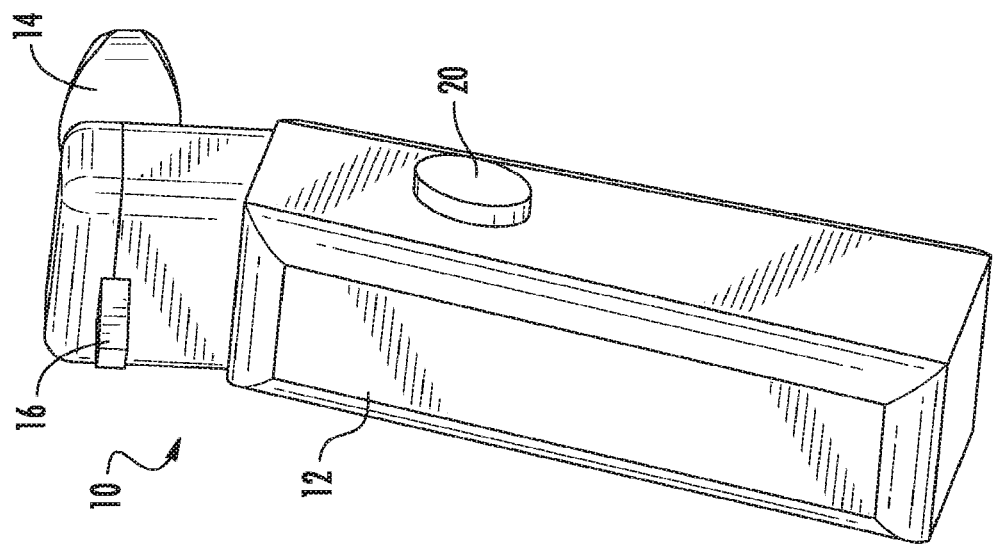
FIGS. 2A-2C illustrate perspective views of the device, according to an embodiment of the present invention.
Figure 2B:
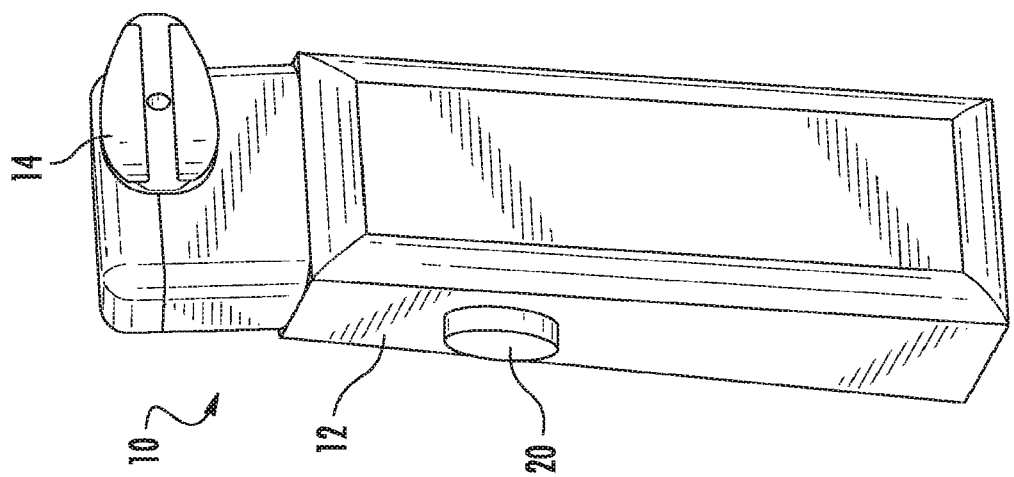
Figure 2A:
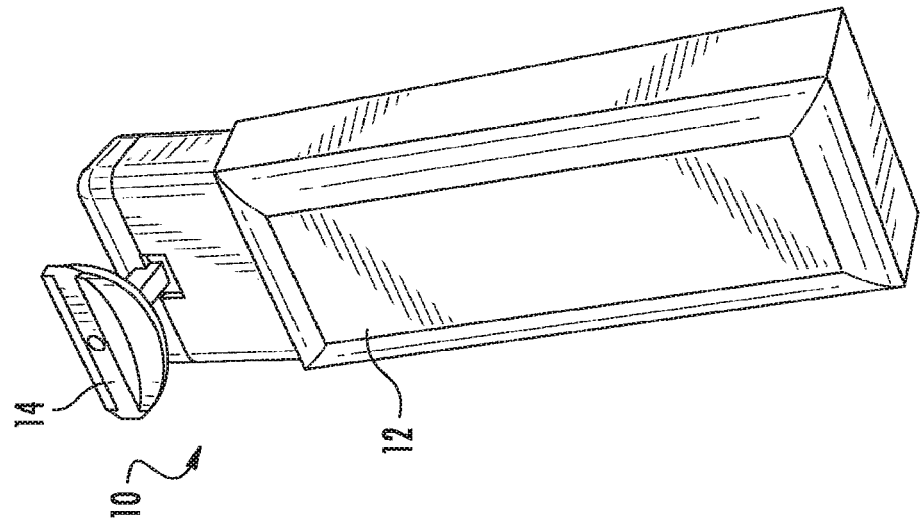
Figure 2D:
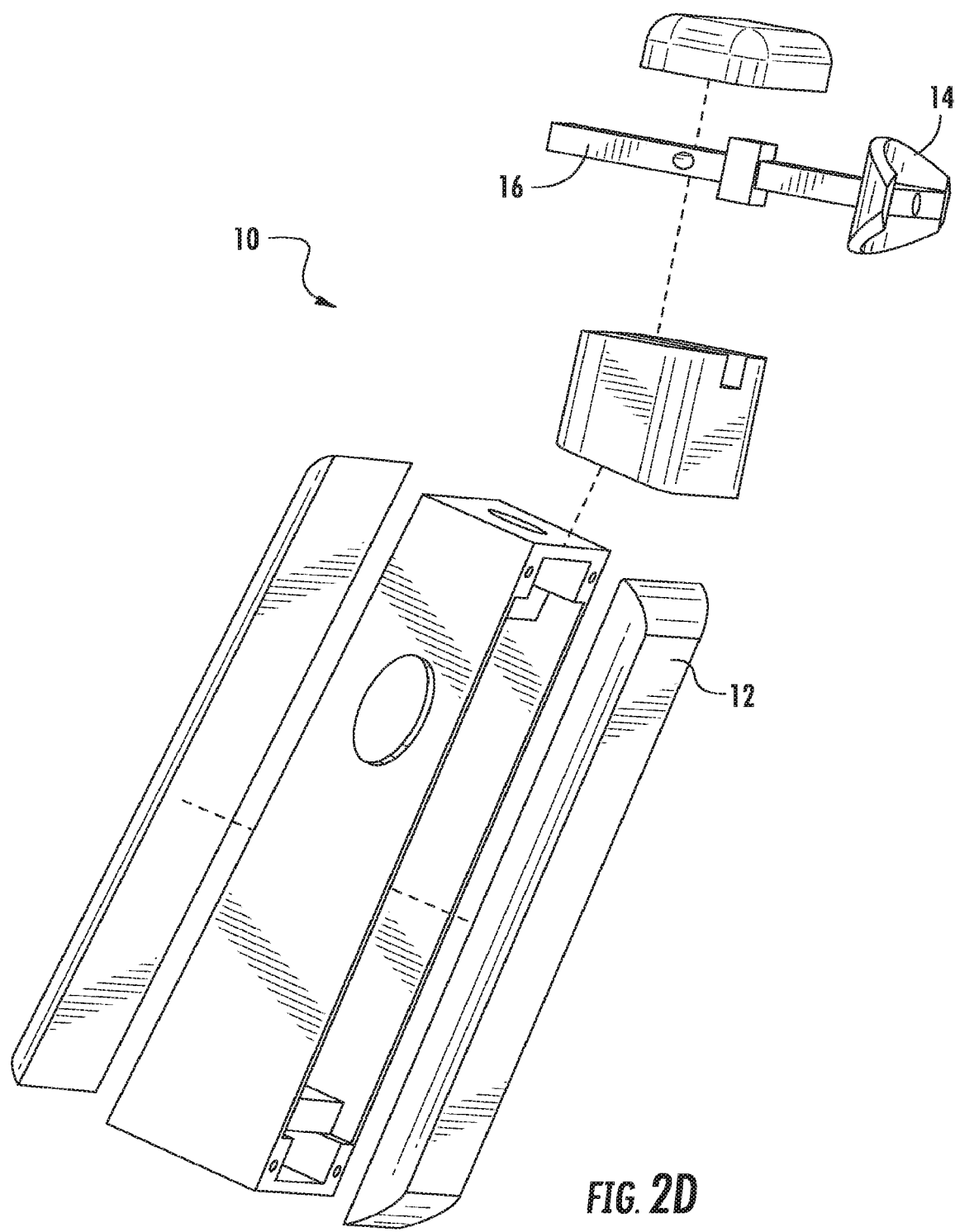
FIG. 2D illustrates an exploded view of the device, according to an embodiment of the present invention.

FIGS. 2A-2C illustrate perspective views of the device, according to an embodiment of the present invention. FIG. 2D illustrates an exploded view of the device, according to an embodiment of the present invention. FIG. 2E illustrates a front-perspective view of the device, according to an embodiment of the present invention. FIG. 2F illustrates a side view of the device, according to an embodiment of the present invention. FIG. 2G illustrates a rear-perspective view of the device according to an embodiment of the present invention. As illustrated in FIGS. 2A-2G, the device 10 includes a body 12 and a mouthpiece 14. The mouthpiece 14 extends out from the body 12, such that it can be placed in the mouth of the user. The mouthpiece 14 can be reusable or disposable and can be coupled to and decoupled from the body 12 of the device 10 using a coupling 16. As illustrated, the coupling 16 takes the form of a peg and hole coupling, however, any suitable means of coupling the mouthpiece 14 to the device 10 known to or conceivable by one of skill in the art could also be used. The coupling 16 is insulated from saliva and attaches the mouthpiece 14 to the device 10 both electrically and physically. The device 10 includes respiration detection microphones 18 positioned on the body 12 of the device 10. The device 10 also includes an on/off button 20 that includes an ECG+ contact, RED and IR LEDs, and an optodetector. The button 20 is positioned on the body 12 of the device 10 such that it is easy for the user to hold down with a thumb or finger while using the device. The mouthpiece 14 includes an ECG− detector 22, an ECGref detector 24, an upper lip optodetector and IR LED 26, and a thermocouple 28. The device 10 also includes a display 30. The display can show a number of things to the user, including but not limited to, instructions, results, and a timer for use of the device.

Figure 4:
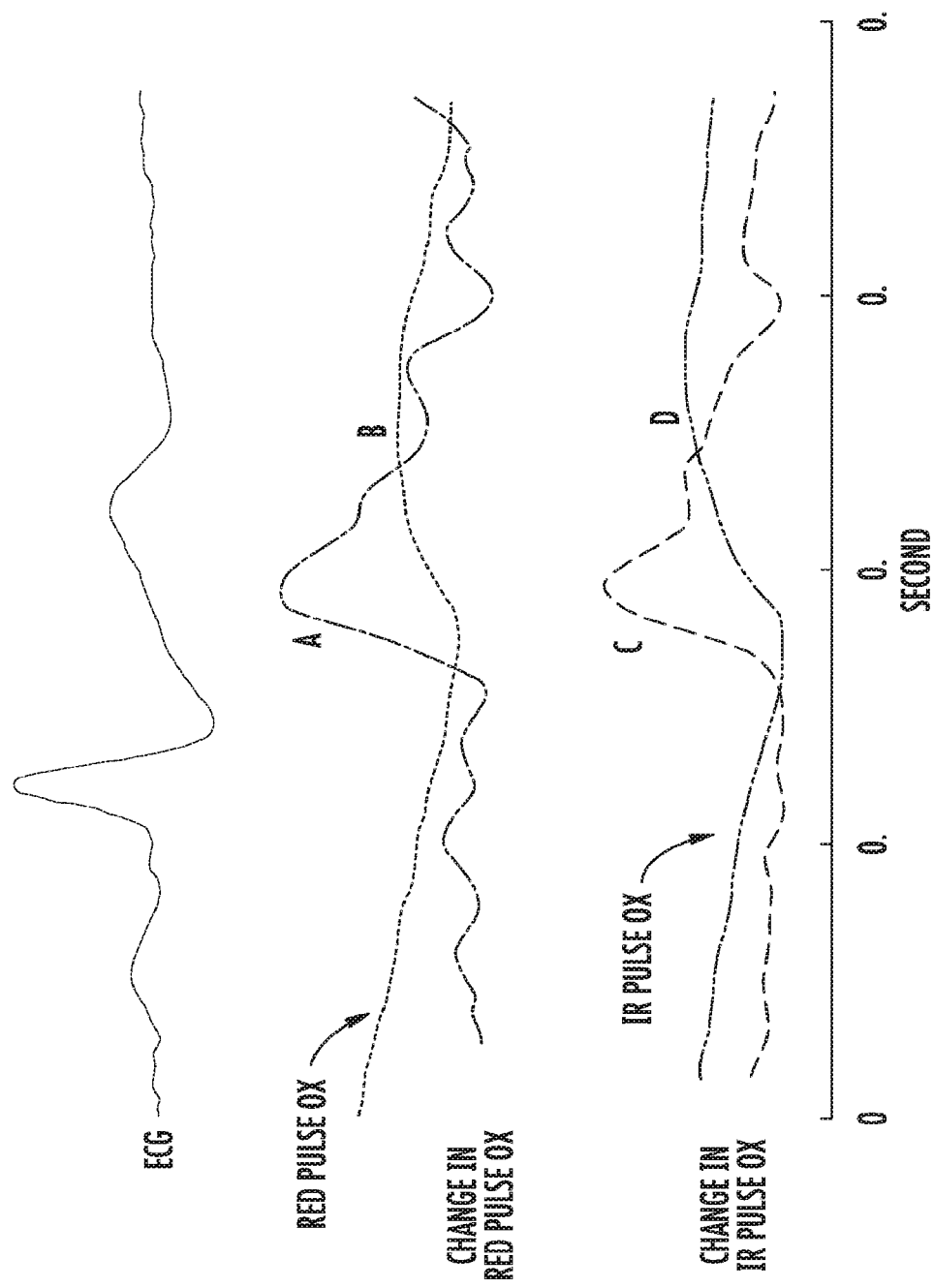
FIG. 4 illustrates a graphical view of parameters used in blood pressure calculation from the lip and thumb blood value and ECG measurements.

FIG. 3A illustrates a graphical view of a sample of typical data collected by sensors on a device according to an embodiment of the present invention. FIG. 3B illustrates a graphical view of a portion of the recording in greater detail. FIG. 4 illustrates a graphical view of parameters used in blood pressure calculation from the lip and thumb blood value and ECG measurements.

The device includes a hand held unit and an individual comfortable mouthpiece. The mouthpiece is clicked into the hand-unit, and the patient holds the unit in the mouth. The device obtains all measurements simultaneously in approximately 30 seconds and displays the final measurements on the hand-unit's display. Special attention is devoted to acquiring blood pressure as it is derived from a combination of sensors. Additionally, the complete dataset including the ECG and pulse oximetry traces are beamed via a cell network, wireless internet connection, RFID protocol, or other means of transmitting data known to or conceivable by one of skill in the art to a cell phone, smartphone, tablet, phablet, personal computer, or directly to a central database in real time, where it becomes immediately accessible by the healthcare provider via at least one of but not limited to a website and a computer application. Any computer software associated with the present invention is programmed onto a non-transitory computer readable medium, which will be described further, herein.

Figure 5:
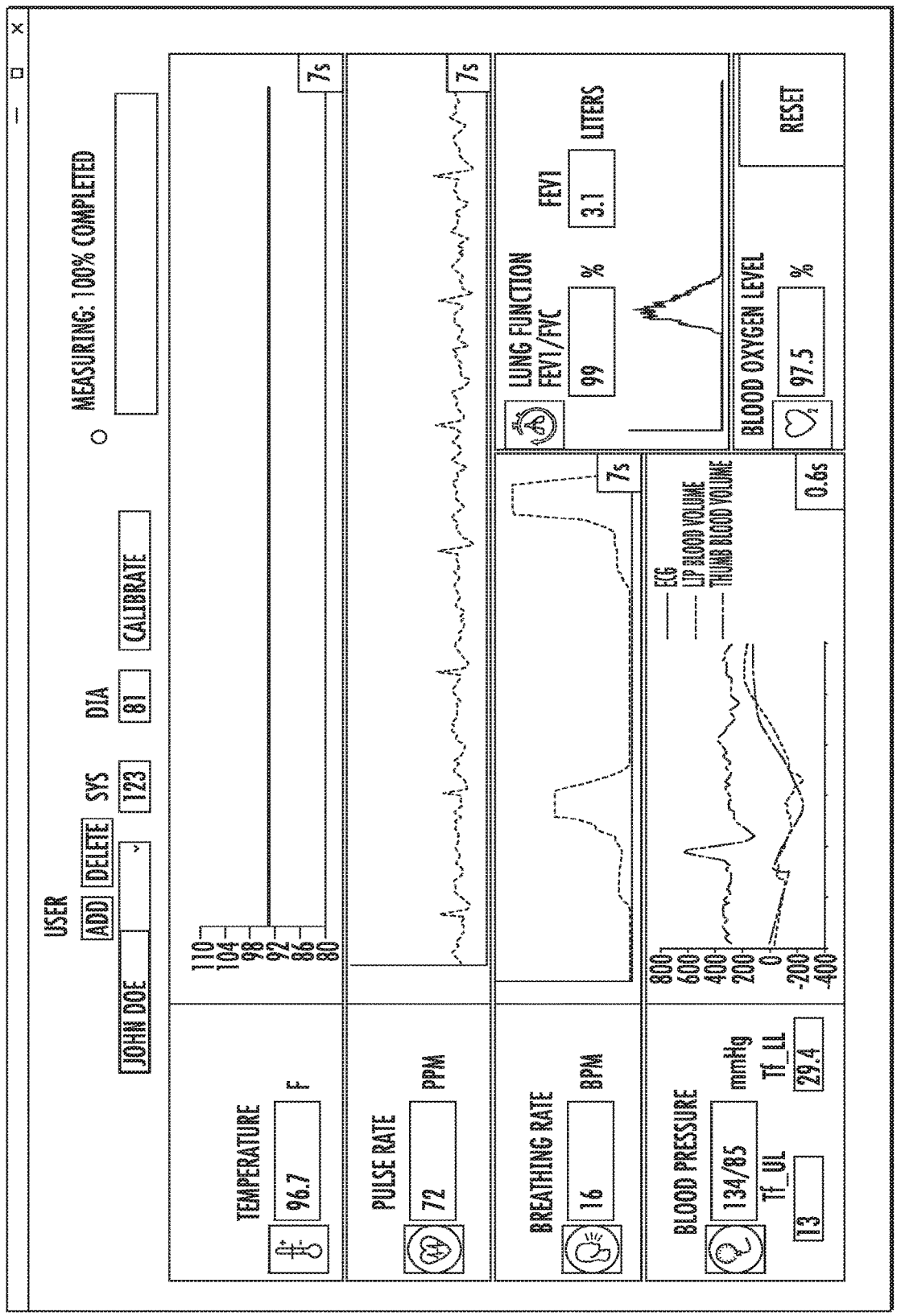
FIG. 5 illustrates an exemplary image of a user interface, according to an embodiment of the present invention.

The user interface can be based on a tablet or smart phone. Alternately, the user interface can be built into the device itself. The calibration function allow the device to notonly be assigned to a particular patient, but also allow the recording of complementary measurements from a calibrated device for comparison to the measurements taken with the MouthLab. FIG. 5 illustrates an exemplary image of a user interface, according to an embodiment of the present invention. The user interface displays information from the MouthLab. The user interface also accepts input from the user regarding the patient. In addition, the user interface can display an indicator of the progress of measurement of the subject's vital signs, such that the user knows when the device can be removed from the mouth and the appendage removed from the sensor.

The patient completes the measurement by ejecting the mouthpiece. The mouthpiece can be discarded or cleaned for reuse by the same patient. The mouthpieces can include color coding or other identifiers known to or conceivable by one of skill in the art, such that more than one person in a household can use the base unit with his or her own separate mouthpiece. Disposable mouthpieces can include labeling as such.

An electronic ID can be attached to every mouthpiece. This tag can be achieved, in a preferred embodiment, by adding an inexpensive random value resistor into every mouthpiece (no diagram for this as it is simply internal to the device with extra two leads that connect it to the hand unit). An inexpensive ID is important, so as to not drive the price of the mouthpiece up, as it is supposed to be low cost. However, any suitable identification tagging known to or conceivable to one of skill in the art could also be used. The hand unit senses the value of this resistor electronically when the mouthpiece is plugged into the unit—this can be achieved with a standard and simple voltage divider circuit that is sampled by the microcontroller. The hand unit will then recognize the mouthpiece as belonging to a particular patient, or allow the user (e.g. nurse) to assign the mouthpiece to a particular patient based on its ID if it has not yet been assigned. This capability will allow the re-use of the mouthpiece by a particular patient and allow for automatic association of the medical information with the specific patient in the database or EMR. This will be very useful in the cases in which one hand unit is used with multiple mouthpieces. For example a nurse in a nursing home walking between rooms and taking measurements of multiple residents using one hand unit and each patient's own mouthpiece.

Breathing rate is detected using the two microphones positioned on the body of the device described above. One microphone is used to acquire exhalation/inhalation pattern from the nose and the other microphone is used to acquire exhalation/inhalation from the mouth after it gets routed through the stem of the mouthpiece.

An additional "Spirometry" microphone can be included to sense strong exhalation from the mouth. Alternately, one of the two microphones positioned on the body of the device can take the form of a spirometry microphone. This is a regular microphone (just like the microphones that monitor breathing), but the sensitivity of the circuit that amplifies the signal from the microphone is intentionally set to low. Whereas the sensitivity of the microphones that detect breathing must be high to be able to detect even faintest breathing, the Spirometry microphone circuit is set to very low sensitivity to be able to measure maximum lung exhalation. This is the microphone that is used to measure FEV1 and FEV1/FVC spirometry parameters (shown under Lung Function on the tablet user interface) to measure asthma and COPD progression. FEV1 is the volume of air exhaled during the first second, and FEV1/FVC is the percent of the lung capacity exhaled over the first second of maximum exhalation. FVC is the total lung volume. To collect these lung capacity measurements after all of the other measurements are collected, the user is prompted to take a deep breath and exhale as hard as possible. An alternate implementation could allow for the use one microphone from the mouth rather than two, but that one microphone's sensitivity (gain) would be controlled by the microcontroller within the hand unit. Another alternative implementation is a high dynamic range microphone and high dynamic range analog to digital converter. Any other suitable solution for measuring strong exhalation known to or conceivable by one of skill in the art could also be used.

Figure 6:
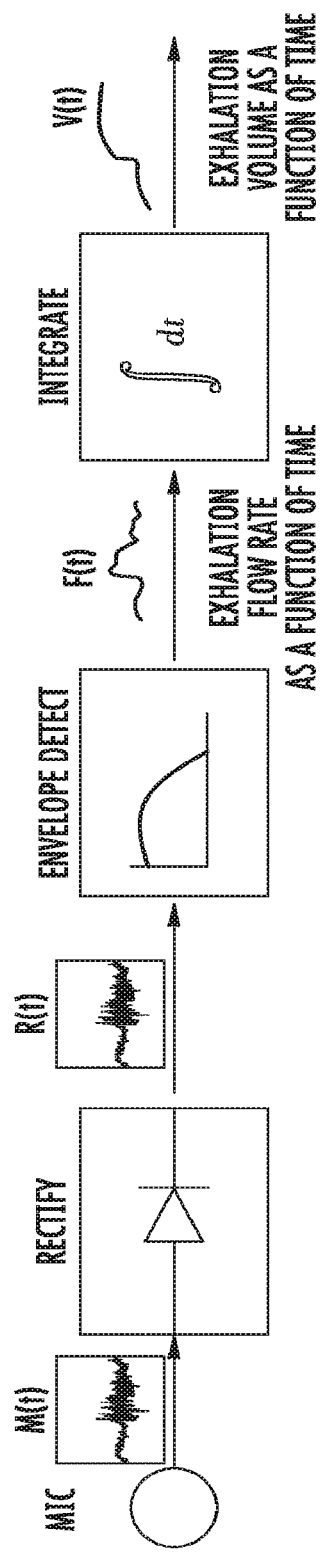
FIG. 6 illustrates a flow diagram of the signal processing necessary for obtaining the lung function measurement.

The signal processing involved in obtaining this measurement for the lung function is the following: The envelope is extracted by low-pass filtering the rectified microphone signal (it can also be obtained via a Hilbert transform as an alternate implementation)—the amplitude of this signal is proportional to the exhaled flow rate, followed by integration of this flow rate with respect to time to obtain the exhaled volume as a function of time. The exhaled volume is then obtained at the first second of exhalation to obtain FEV1=V(t=1 s) and then we divide this number by the total exhaled volume at ~6 s FVC=V(t=6 s) to obtain FEV1/FVC. FIG. 6 illustrates a flow diagram of the signal processing necessary for obtaining the lung function measurement.

ECG is detected using the standard three-lead ECG via three metal electrodes (ECG−, ECG+, and ECGref). Instead of the electrodes being positioned on the leg and the trunk of the body however, the ECG+ electrode is positioned on the thumb-on-off-button, with the ECG− and ECGref electrodes positioned on the mouthpiece. Temperature is detected using a thermocouple positioned on the bottom of the mouthpiece. Pulse oximetry is captured using the infrared (IR) and red (RED) LEDs positioned on the thumb-on-off-button. As in a standard pulse-ox detection scheme, the blood oxygen level is monitored by the relative absorbance of the light intensity in the RED led spectrum that is affected by oxygenated hemoglobin concentration as compared to the intensity of IR wavelength that is not affected by hemoglobin levels. The innovative step here is that the light is monitored through reflection rather than passing through the tissue. Having the optodetector and the LEDs on the same side of the finger rather than shining through allows for simpler design of the device and the measurement from being affected by the variability of thumb thickness. To keep the thumb from pressing on the button too hard and cutting off blood flow, the button pressure is countered by a spring positioned on a back side of the button. When the thumb compression exceeds the pressure at which the blood flow is affected, the patient is alerted to reduce the pressure on the button.

Pulse rate is measured by the inverse of the periodicity of the ECG or pulse-ox signal. Blood pressure is monitored as a function of 10 parameters that reflect the post-heart-contraction blood flow through the upper lip and the finger. Conceptually, different blood pressure will affect the rate and duration of blood flow to the upper lip versus the rate and duration of blood flow to the thumb following heart contraction. Heart contraction is monitored using the ECG waveform described earlier. The upper lip blood volume is monitored by IR led and optodetector on the mouthpiece. The thumb blood volume is monitored by the IR led and the optodetector positioned on the thumb-on-off-button.

If the time-varying blood volume of the upper lip is denoted as VL(t) and the time varying blood volume in the thumb as VT(t), then to preprocess the data, both are normalized as:

$$VL\_AC(t)=VL(t)-\text{mean}(VL(t))$$

$$VL\_\text{norm}(t)=VL\_AC(t)/(\max(VL\_AC(t))-\min(VL\_AC(t)))$$

And $$VT\_AC(t)=VT(t)-\text{mean}(VT(t))$$

$$VT\_\text{norm}(t)=VT\_AC(t)/(\max(VT\_AC(t))-\min(VT\_AC(t)))$$

The derivatives of both normalized functions VL_norm(t) and VT_norm(t) are taken to obtain dVL_norm(t) and dVT_norm(t). The derivatives indicate blood flow rate (rather than the blood volume). In the figure, VL_norm(t) and VT norm(t) are shown in red and the corresponding dVL_norm (t) and dVT norm(t) are shown in black.

The various parameters from these four waveforms indicate the dynamics of the blood flow. There are five parameters obtained for the finger blood flow and the lip blood flow. Four of these parameters are illustrated in the figure for the upper lip. A, indicates the time at which the blood starts to fill. B is the time of maximum flow rate, C is the maximum flow rate, and D is the duration of flow (defined as the time it takes to reach 14 of the 10 maximum flow rate). The fifth parameter, E, not illustrated in the figure, is the total area under the volume curve. Therefore, there are 10 parameters total that describe the blood flow dynamics following the heart contraction (5 for the upper lip and 5 for the thumb).

To find systolic and diastolic blood pressure, a neural network trained on the datasets from 10-20 patients is used. This artificial neural network uses back-propagation as a training method. The neural network includes 10 input nodes (for each of the 10 parameters), 26 hidden nodes, and 2 output nodes (for the systolic and diastolic blood pressure). Once the network has been trained, the algorithm is used on all subsequent patients.

It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, RFID, or any other suitable data transmission means known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for measuring vital signs of a user comprising:
    a device body configured to be held by the user's left hand and having an on/off switch positioned and configured to be contacted by the user's left thumb, wherein the on/off switch includes an ECG+ contact, a RED LED, an IR LED, and an optodetector;
    a mouthpiece that is coupled to the device body, wherein the mouthpiece includes an ECG– contact, an ECGref contact, an upper lip optodetector, and an IR LED;
    a connector for coupling the mouthpiece to the device body, wherein the connector is insulated from saliva, and attached the mouthpiece to the device body both electrically and physically.

2. The device of claim 1 wherein the device further comprises at least one additional sensor and the device is further configured to simultaneously obtain two or more vital signs selected from a group consisting of breathing rate, blood pressure, temperature, electrocardiogram, pulse rate, blood oxygen levels, blood sugar levels, respiration biochemical analysis, saliva biochemical analysis, and metabolic rate.

3. The device of claim 2 wherein the at least one additional sensor comprises at least one selected from a group consisting of a microphone and thermocouple.

4. The device of claim 3 wherein the microphone is positioned on the device body.

5. The device of claim 3 wherein the microphone is configured to be set with one sensitivity.

6. The device of claim 3 further comprising a pair of microphones having different sensitivities.

7. The device of claim 3 further comprising the microphone being configured with variable sensitivity.

8. The device of claim 3 wherein the microphone further comprises a high-dynamic range microphone.

9. The device of claim 8 further comprising a high-dynamic range analog to digital converter.

10. The device of claim 1 further comprising a computing device with a non-transitory computer readable medium programmed to store and transmit data related to the vital signs.

11. The device of claim 10 wherein the computing device is configured to be networked to a smartphone for transmitting the data to a server for processing.

12. The device of claim 11 wherein the computing device is further configured to make the data transmitted to the server accessible to a computer application for use by a physician.

13. The device of claim 1 further comprising a user display.

14. The device of claim 13 wherein the user display is configured to show at least one selected from a group consisting of instructions, data acquisition time required, results, and testing being completed.

15. The device of claim 13 further comprising the user display being incorporated into the device body.

16. The device of claim 13 wherein the user display is positioned on a computing device remote from the device body configured to transmit information to and receive information from the device for measuring vital signs.

17. The device of claim 10, wherein the non-transitory computer readable medium is encoded with one or more computer programs for obtaining a measurement of blood pressure, the one or more computer programs including:
    an ECG detecting module in communication with the ECG– contact, the ECG+ contact, and the ECGref contact, the ECG detecting module configured to monitor an ECG waveform;
    an IR LED detecting module in communication with the RED LED, the IR LED, and the optodetector of the on/off switch and the IR LED and the upper lip optodetector of the mouthpiece, the IR LED detecting module configured to monitor a lip blood volume, a lip blood flow rate, a thumb blood volume, and a thumb blood flow rate; and a blood pressure calculation module configured to monitor a lip blood flow duration and a thumb blood flow duration and to compare the lip blood flow duration and the lip blood flow rate to the thumb blood flow duration and the thumb blood flow rate.

* * * * *